(12) United States Patent
Stahl

(10) Patent No.: US 8,229,071 B2
(45) Date of Patent: Jul. 24, 2012

(54) GATED BURST MODE RADIATION TREATMENT OF MOVING TARGETS

(75) Inventor: Johannes N. Stahl, Walnut Creek, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 34 days.

(21) Appl. No.: 12/972,193

(22) Filed: Dec. 17, 2010

(65) Prior Publication Data

US 2012/0008745 A1     Jan. 12, 2012

Related U.S. Application Data

(63) Continuation of application No. 12/834,067, filed on Jul. 12, 2010.

(51) Int. Cl.
*A61N 5/10* (2006.01)
(52) U.S. Cl. .......................................................... 378/65
(58) Field of Classification Search .................... 378/62, 378/65, 95, 145, 147, 150, 151
See application file for complete search history.

(56) References Cited

U.S. PATENT DOCUMENTS

| | | | |
|---|---|---|---|
| 5,818,902 A | 10/1998 | Yu | |
| 7,469,035 B2 | 12/2008 | Keall et al. | |
| 7,609,810 B2 | 10/2009 | Yi et al. | |
| 7,983,380 B2 * | 7/2011 | Guertin et al. | 378/4 |
| 2005/0054916 A1 | 3/2005 | Mostafavi | |
| 2008/0226030 A1 | 9/2008 | Otto | |
| 2008/0243018 A1 | 10/2008 | Zuhars et al. | |
| 2009/0041200 A1 | 2/2009 | Lu et al. | |
| 2010/0183120 A1 | 7/2010 | Nord et al. | |
| 2010/0189220 A1 * | 7/2010 | Flynn et al. | 378/65 |
| 2010/0329422 A1 * | 12/2010 | Brown et al. | 378/65 |
| 2011/0080990 A1 * | 4/2011 | Filiberti et al. | 378/4 |
| 2011/0200170 A1 * | 8/2011 | Nord et al. | 378/65 |

FOREIGN PATENT DOCUMENTS

| | | |
|---|---|---|
| GB | 2 441 550 | 3/2008 |
| WO | WO 2007/012185 | 2/2007 |

OTHER PUBLICATIONS

Silke Ulrich et al., "Development of an optimization concept for arc-modulated cone beam therapy", Physics in Medicine and Biology, 52 (2007), IOP Publishing, doi:10.1088/0031-9155/52/14/2006, (pp. 4099-4119, 21 pages total).
EP Search Report in related EP application No. EP 11 17 3319, dated Oct. 25, 2011, 7 pages total.

(Continued)

*Primary Examiner* — Irakli Kiknadze

(57) ABSTRACT

Some aspects include a system, apparatus, and method for obtaining a burst mode treatment plan to be administered by a radiotherapy device, the burst mode treatment plan prescribing parameters for one or more dynamic axes, parameters for one or more static axes, and position parameters for the one or more dynamic axes corresponding to a prescribed delivery period of burst mode irradiation; receiving an indication of occurrences of a substantially periodic treatment opportunity for a target volume of a patient from a gating device, the treatment opportunity being a period of time the target volume is in a position to be irradiated according to the burst mode treatment plan; synchronizing the treatment opportunity and the prescribed delivery period of burst mode irradiation; and irradiating the target volume during the synchronization of the treatment opportunity and the prescribed delivery period of burst mode irradiation.

22 Claims, 6 Drawing Sheets

OTHER PUBLICATIONS

Oliver, et al. *Experimental measurements and Monte Carlo simulations for dosimetric evaluations of intrafraction motion for gated and ungated intensity modulated arc therapy deliveries; IMAT deliveries with motion management*, Physics in Medicine and Biology, Taylor and Francis Ltd., London, GB, vol. 53, No. 22, Nov. 21, 2008, pp. 6419-6436, XP020141511, ISSN 0031-9155, DOI: 10.1088/0031-9155/53/22/010.

EP Search Report in counterpart EP application No. EP 11 17 3380, dated Oct. 18, 2011, 10 pages total.

* cited by examiner

GATED BURST MODE RADIATION TREATMENT OF MOVING TARGETS

CROSS REFERENCE TO RELATED APPLICATION

This is a continuation of co-pending prior U.S. patent application Ser. No. 12/834,067 filed on Jul. 12, 2010 and entitled, ROTATIONAL RADIATION TREATMENT OF MOVING TARGETS and corresponding to.

BACKGROUND

1. Field

The embodiments described below relate generally to delivery of radiotherapy treatment. More specifically, some embodiments are directed to controlling dynamic and static axes during radiation treatment of moving targets and systems for delivering such treatments.

2. Description

Radiotherapy or radiation therapy is used to treat cancer and other diseases with ionizing radiation. Conventional radiotherapy systems generate and direct a beam of radiation to a targeted treatment volume within a patient. The radiation beam is intended to injure or destroy cells within the target volume by causing ionizations within the cells or other radiation-induced cell damage.

Radiotherapy treatment plans for delivering radiation to a patient are intended to maximize radiation delivered to a target area, while minimizing the radiation delivered to surrounding healthy tissue. In this regard, the treatment of a moving target area poses a challenge to radiotherapy, including the accuracy with which the target area will be radiated as compared to a static target area. In the context of radiotherapy treatments, the treatment of moving targets is further complicated due to the movement of the gantry and other components of the radiotherapy apparatus and/or the patient. Such radiotherapies include but are not limited to Arc-Modulated ConeBeam Therapy, Intensity Modulated Arc Therapy, and a variety of other radiotheraopy treatment schemes that involve rotating a linear accelerator (LINAC) gantry or other motorized axis about the patient and delivering radiation to a targeted patient area from a number of different gantry angles. In some contexts, the delivery of the treatment radiation may be either continuous or at discrete locations.

One conventional method for addressing the delivery of radiation treatment to moving targets includes using an increased margin of delivery around a target that is large enough to account for target excursions from a nominal position. While the increased margin may result in the target receiving a desired radiation dose, surrounding healthy tissue or organs are at an increased risk of also receiving radiation. Gated treatment techniques to address moving targets involve determining a gating window during which the target movement is minimized to deliver the radiation treatment. For example, radiation may be delivered to the target only when the patient is within 80% exhalation of the breathing cycle, a period when motion of the targeted treatment area may be relatively motionless. However, acquisition of planning images (e.g., 4D CT computed tomography) and a breathing monitoring device to provide an indication of the phases of the patient's breathing cycle are needed for this technique. One proposed technique for delivering radiation to a moving target involves using an auxiliary device to determine the location and the shape of the target at any point in time and reshaping a beam shaping device (e.g., a MLC or multileaf collimator leaves) of the radiotherapy system to follow (i.e., track) the target shape at any point in time. However, this technique also requires an auxiliary device in addition to the radiotherapy system.

The present inventor has realized that conventional radiation treatments are inefficient and insufficient for radiotherapy treatment involving moving aspects of a radiotherapy system and moving targets. Accordingly, other methods and systems to provide radiation treatment of moving components of a radiotherapy system and moving target areas are desired.

SUMMARY

In order to address the foregoing, some embodiments provide a system, method, apparatus, and means for obtaining a burst mode treatment plan to be administered by a radiotherapy device, the burst mode treatment plan prescribing parameters for one or more dynamic axes, parameters for one or more static axes, and position parameters for the one or more dynamic axes corresponding to a prescribed delivery period of burst mode irradiation; receiving an indication of occurrences of a substantially periodic treatment opportunity for a target volume of a patient from a gating device, the treatment opportunity being a period of time the target volume is in a position to be irradiated according to the burst mode treatment plan; synchronizing the treatment opportunity and the prescribed delivery period of burst mode irradiation; and irradiating the target volume during the synchronization of the treatment opportunity and the prescribed delivery period of burst mode irradiation.

The appended claims are not limited to the disclosed embodiments, however, as those in the art can readily adapt the descriptions herein to create other embodiments and applications.

BRIEF DESCRIPTION OF THE DRAWINGS

Embodiments will become readily apparent from consideration of the following specification as illustrated in the accompanying drawings, in which like reference numerals designate like parts, and wherein.

DETAILED DESCRIPTION

The following description is provided to enable a person in the art to make and use some embodiments and sets forth the best mode contemplated by the inventors for carrying out some embodiments. Various modifications, however, will remain readily apparent to those in the art.

Figure 1:
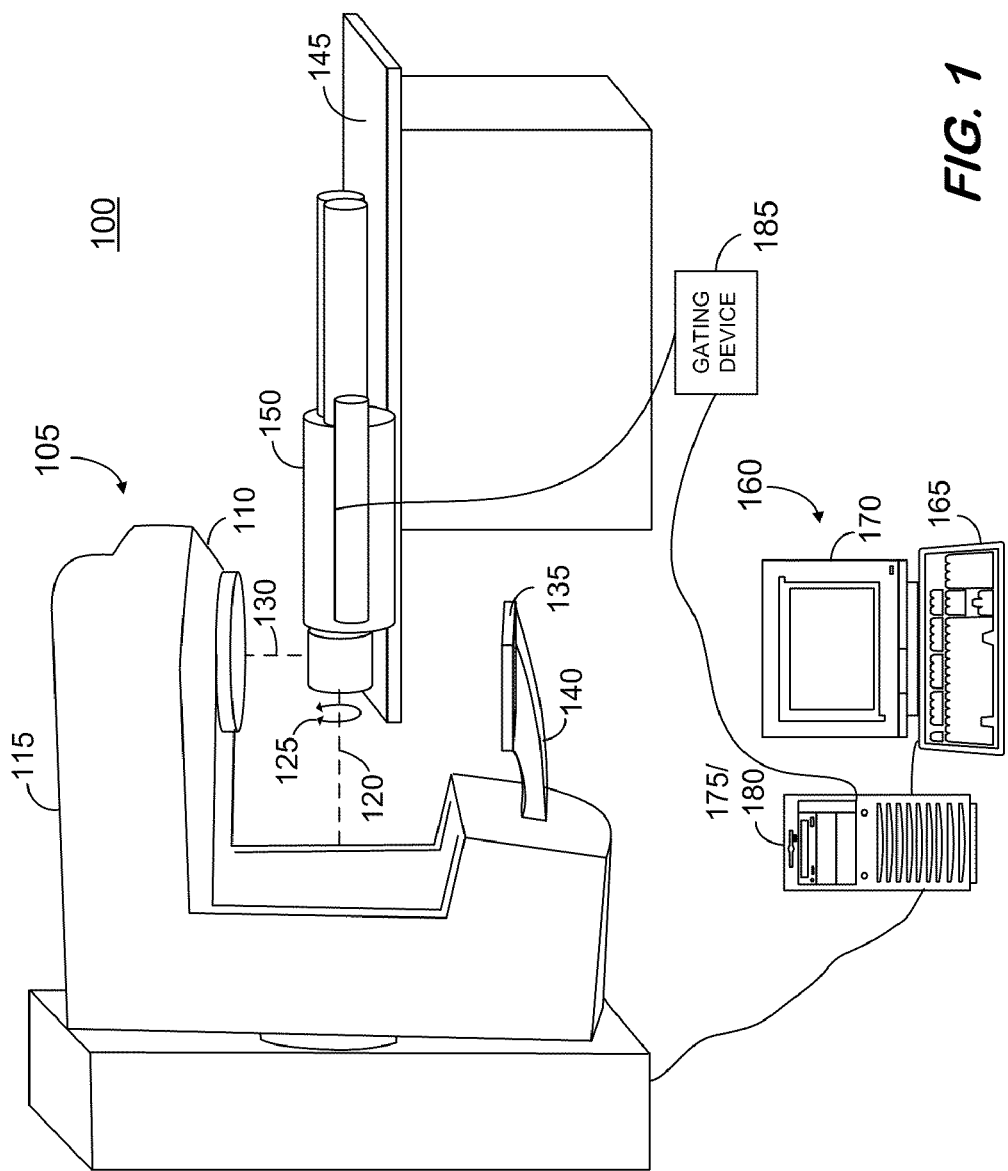
FIG. 1 is a perspective view of a treatment room according to some embodiments.

FIG. 1 illustrates radiotherapy treatment room 100 pursuant to some embodiments. Radiotherapy treatment room 100 includes linear accelerator (linac) 105, table 145 and operator console 160. The various components of radiotherapy treatment room 100 may be used to deliver a beam of radiation to an object such as patient 150. The patient may be positioned to receive the beam according to a radiation treatment plan. The elements of treatment room 100 may be employed in other applications according to some embodiments.

Linac 105 generates and emits a radiation beam (e.g., an x-ray beam) from treatment head 110. The radiation beam may comprise electron, photon or any other type of radiation. According to some embodiments, the beam exhibits energies in the megavoltage range (i.e. >1 MeV) and may therefore be referred to as megavoltage beam. In some embodiments, LINAC 105 may emit a radiation beam in relatively short bursts of time with a relatively high intensity. As an example, high intensity may refer to 10 GY/min and higher, where 20 Gy/min is typical, although higher intensities may be used. In some embodiments, a typical burst time duration may be about (0.5-2.0) seconds, although in some embodiments it may be longer or shorter.

Treatment head 110 is coupled to a projection of gantry 115. Gantry 115 is controllable to be rotatable around gantry axis 120. As indicated by arrow 125, gantry 115 may rotate clockwise or counter-clockwise according to some embodiments. Rotation of gantry 115 serves to rotate treatment head 110 around axis 120. Gantry 115 may also, in some aspects, be moveable in other directions other than or in addition to that indicated by arrow 125.

During radiation emissions (e.g., treatment, imaging, calibration, and other procedures) treatment head 110 emits a divergent beam of megavoltage x-rays along beam axis 130. The beam is emitted towards the isocenter of linac 105. The isocenter may be located at the intersection of beam axis 130 and gantry axis 120. Due to divergence of the beam and the shaping of the beam by beam-shaping devices in treatment head 110, the beam may deliver radiation to a volume of patient 150 rather than only through the isocenter.

Table 145 may support a patient during radiation treatment and other aspects discussed herein. Table 145 may be adjustable to assist in positioning patient 150 or a particular target area and volume of the patient at the isocenter. Table 145 may also be used to support devices used for such positioning, for calibration and/or for verification. In some embodiments, table 145 may be selectively moved during at least portions of a radiation treatment, in accordance with a treatment plan.

Imaging device 135 may comprise any system to acquire an image based on radiation received at the imaging device. Imaging device 135 may be attached to gantry 115 in any manner, including an extendible and retractable (i.e., moveable) housing 140. Rotation of gantry 115 may cause treatment head 110 and imaging device 135 to rotate around the isocenter such that the isocenter remains located between treatment head 110 and imaging device 135 throughout stationary and rotational movements of gantry 115.

Imaging device 135 may acquire projection images before, during and/or after radiation treatment. In some embodiments, imaging device 135 may include an analog or a digital radiation detector. Imaging device 135 may be used to acquire images based on radiation emitted from treatment head 110. These images may reflect the attenuative properties of objects located between treatment head 110 and imaging device 135. Such projection images may be used to determine imaging geometry parameters associated with the imaging system comprising treatment head 110 and imaging device 135. The two-dimensional projection images and/or three-dimensional images reconstructed based on the projection images may be used to detect, monitor, and record a target area or volume (e.g., a tumor) position and a movement of the target area or volume.

Operator console 160 includes input device 165 for receiving instructions from an operator such as an instruction to calibrate linear accelerator 105 and an instruction to configure the beam shaping device of treatment head 110 (e.g., a collimator) with a particular field of view for a particular interval of time. Console 160 also includes output device 170 that may include a monitor for presenting acquired three-dimensional images, operational parameters of linear accelerator 105 and/or interfaces for controlling elements thereof. Input device 165 and output device 170 are coupled to processor 175 and storage 180.

Effective treatment of moving targets includes detecting and monitoring the motion of a target area, and delivering radiotherapy beams to the moving target. A number of conventional technologies may be used to detect and monitor target motion. Some techniques include providing a device to monitor the rise and fall of an external surface of the patient caused by breathing. Such devices may include a belt that holds a strain-gauge against a patient's moving chest and/or abdomen, wherein the strain-gauge produces a signal corresponding to the rise and fall of the patient's chest/abdomen. Some other techniques include optical mechanisms that monitor external fiducial markers attached to the patient's skin and produce a signal corresponding to the rise and fall of the patient's chest/abdomen. Some other techniques include providing implantable beacon devices in a patient to directly monitor and detect tumor motion without a surrogate. Further technologies for monitoring the motion of a patient area targeted for radiotherapy treatment include using real-time imaging based systems such as, for example, a fluoroscopy imaging systems and magnetic resonance (MR) imaging systems.

Gating device 185 includes an apparatus, device, or system to determine and provide an indication, such as a signal, of whether a target area of patient 150 is in a position to be irradiated by a treatment beam, as prescribed by a treatment plan. In some instances the gating device may provide a signal indicative of the position of a target volume in the patient and processor 175 further determines whether the target volume is in a position to be irradiated by the treatment beam as prescribed by the treatment plan. Gating device 185 may use a variety of methods, mechanisms, and operations to determine an acceptability of the positioning of the target volume. In some instances, the criteria for determining the acceptability of the target position may be set by a user.

In some aspects, the gating device may be used to acquire data regarding the movement of the target volume before and during the administration of a radiation treatment. In some embodiments, data acquired by gating device 185, through either direct or indirect observation and monitoring of patient 150, may be used to determine a statistical model of the movement of the target volume. In some embodiments, the acquisition of target volume motion may provide a historical set of data from which the statistical model of the movement of the target volume may be derived. Accordingly, a statistical model of the movement of the target volume can be determined that describes, based on a history of acquired breathing cycle data, where the occurrence of a future breathing cycle may be predicted. In some aspects, gating device 185 may indicate and/or determine the time during which the target volume is in an acceptable position for being irradiated with the treatment beam, where the acceptable position may correspond to a point position, a range of positions, and a time period.

The time during which the target volume is in the acceptable position for being irradiated with the treatment beam is referred to herein as a treatment opportunity. In some embodiments, the treatment opportunity is substantially periodic based on the movement of the target volume being primarily attributed to the breathing cycles of patient 150. Gating device 185 may provide the indication of the treatment opportunity to processor 180. Embodiments herein include a gated treatment device that is defined as a radiotherapy treatment device (e.g., system 100) that is interfaced with a gating device or at least supplied with data representative of gating device outputs and is controlled to administer a radiation treatment beam in a burst mode during a treatment opportunity (i.e., beam ON condition).

Processor 175 executes program code according to some embodiments. The program code may be executable to control linear accelerator 105 to operate as described in various methods and processes herein. The program code may be stored in storage 180, which may comprise one or more storage media of identical or different types, including but not limited to a fixed disk, a floppy disk, a CD-ROM, a DVD-ROM, an optical disk, a magnetic tape, a solid state storage device, a flash drive, and a signal. Storage 180 may store, for example, initial imaging geometry parameters, radiation treatment plans, projection images, software applications to calibrate linear accelerator 105 and/or to provide radiation treatment, and other data used to perform radiation treatment.

Operator console 160 may be located apart from linear accelerator 105, such as in a different room, in order to protect its operator from radiation. For example, linear accelerator 105 may be located in a heavily shielded room, such as a concrete vault, which shields the operator from radiation generated by accelerator 105.

Each of the devices shown in FIG. 1 may include fewer or more elements than those shown and are not limited to the devices shown in FIG. 1.

Figure 2:
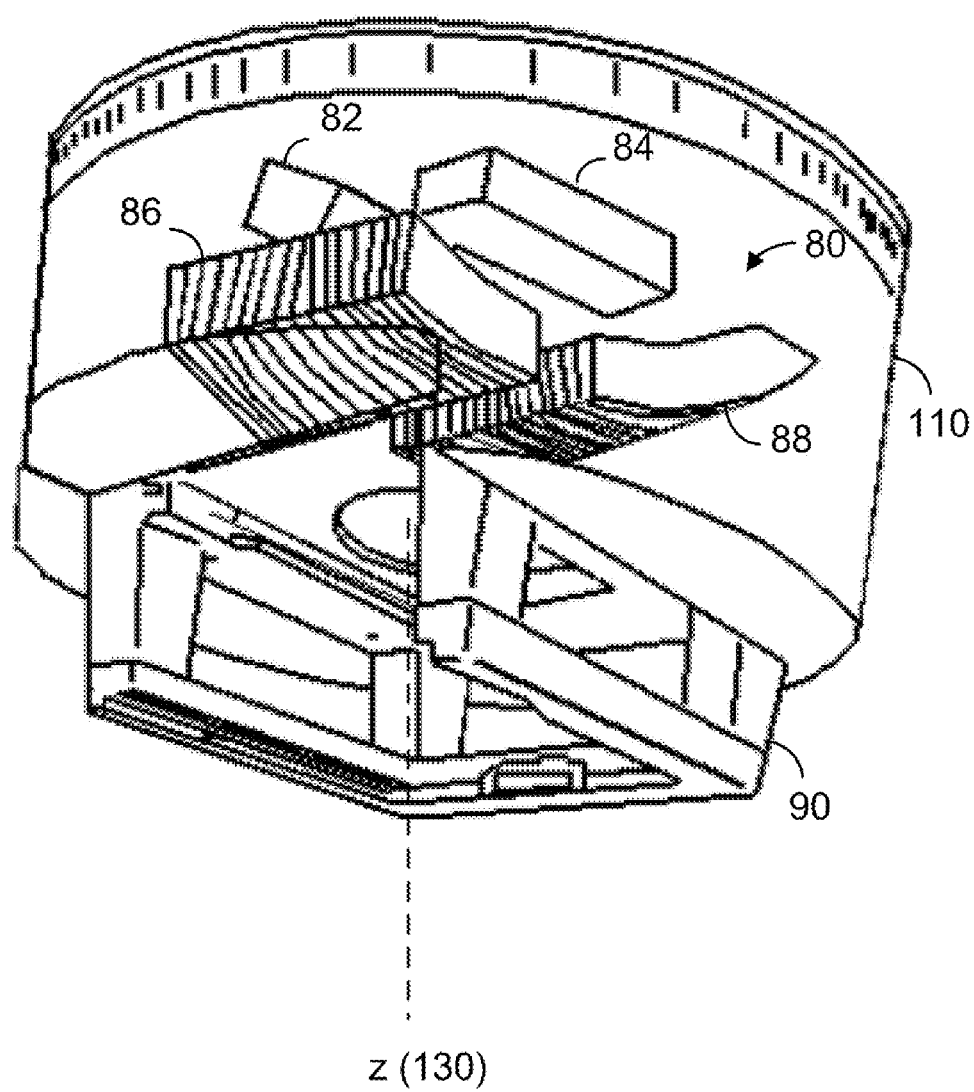
FIG. 2 is a depiction of a beam shaping device in accordance with some embodiments.

FIG. 2 illustrates treatment head 110 according to some embodiments. Treatment head 110 includes a beam shaping device, collimator 80, that may be used to shape a radiation beam to conform to an aperture specified by a treatment plan. Collimator 80 includes a pair of jaws (Y-jaws) 82 and 84 and a pair of jaws (X-jaws) 86 and 88. The positioning of X-jaws 86 and 88 and Y-jaws 82 and 84 determines a size and shape of an opening (i.e, a field of view) through which a radiation beam may pass along axis 130.

Each pair of jaws 86/88 and 82/84 is rotatable about axis 130. As depicted in FIG. 2, X-jaws 86 and 88 may be formed of a plurality of individual elements. These individual elements may be movable along a path intersecting axis 130. Movement of each element may be individually controllable to generate a wide variety of aperture shapes.

Treatment head 110 also includes accessory tray 90. Accessory tray 90 may be configured to receive and securely hold attachments used during the course of treatment planning and treatment (such as, for example, reticles, wedges, or the like). According to some embodiments, treatment head 110 is rotatable to rotate collimator 80 and accessory tray 90 around axis 130 while maintaining the physical relationships between X-jaws 86 and 88, Y-jaws 82 and 84, and accessory tray 90.

In some embodiments, radiotherapy planning for radiation treatment including moving components of the radiotherapy system components (e.g., a gantry, a support table or couch, etc.) and the moving target includes gate-acquisition computed tomography (CT) imaging to monitor the motion of the breathing of a patient that is to receive rotational radiation treatment. The CT acquisition may be performed in a variety of manners, including processes now known and those that become known in the future. In some aspects, the CT images may be acquired using a breath-hold at a particular phase of the breathing cycle that is deemed acceptable for radiation treatment purposes (e.g., at maximum exhale of the breathing cycle). In some aspects, four-dimensional CT (4D CT) acquisition that provides a CT volume of each phase of the breathing may be used to monitor the motion of the patient area, where the breathing cycle is divided into a number of phases (e.g., 10-16 phases). Based on the acquired images, a treatment planning clinician may decide during which phase(s) of the breathing the treatment radiation should be delivered to the patient. In another aspect, a respiratory device may be configured to acquire a CT volume only at a specific phase of the breathing cycle, such as maximum exhale.

In accordance with aspects herein, a CT volume of the targeted patient area may be acquired in a state, phase or portion of the breathing or other periodic motion of the patient area that is determined to be appropriate for the delivery of the treatment radiation. This acquired CT data may be used as a basis for the development of a radiotherapy treatment plan.

Figure 3:
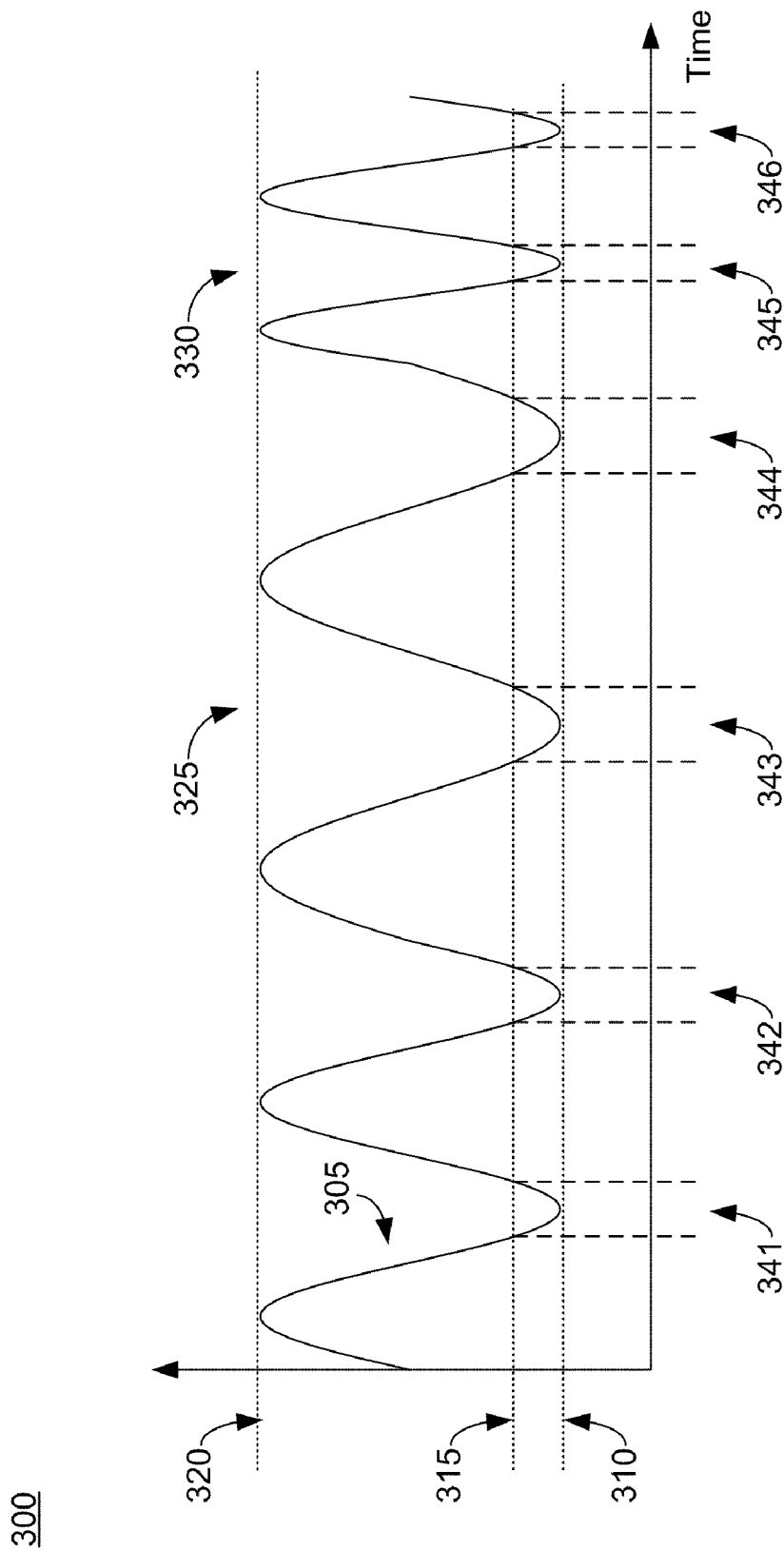
FIG. 3 is an illustrative depiction of a respiratory signal of a patient.

FIG. 3 provides an illustrative example of a respiratory signal 305, in accordance with some embodiments herein. While respiratory signal 305 is hypothetical, it is representative of a respiratory monitoring signal that may be derived from CT images and volumes and/or other data of a patient acquired during a radiotherapy treatment planning process and/or radiation treatment. Respiratory signal 305 illustrates a plurality of breathing cycles, wherein the breathing cycles vary between 100% exhalation at line 310, 80% exhalation at line 315, and 100% inhalation at line 320 over a period of time. It is noted that the time interval between 80% exhalation and 100% exhalation may be specified as the portion, phase or period of the breathing cycle for delivery of radiation treatment due to the relatively static motion a patient target volume may experience during this period of the breathing cycle, however embodiments are not thus limited. Again, the period of time designated for delivery of treatment radiation is referred to herein as a treatment opportunity. In the example of FIG. 3, the treatment opportunity corresponds to the time period the breathing cycle is between 80% and 100% exhalation. That is, treatment opportunities are depicted in FIG. 3 at the time intervals 341, 341, 343, 344, 345, and 346. In some aspects, the treatment opportunity is selected based on, at least in part, the targeted patient area having an acceptable magnitude of motion. The acceptable magnitude of motion is preferably low so as not to compromise the radiotherapy treatment goals. The treatment opportunity may be defined by the burst mode treatment plan.

As shown, the breathing is slower at region 325 than the breathing depicted at region 330. Such variances of the periodic breathing, and thus a patient area movement, may be accounted for in some embodiments herein.

Figure 4:
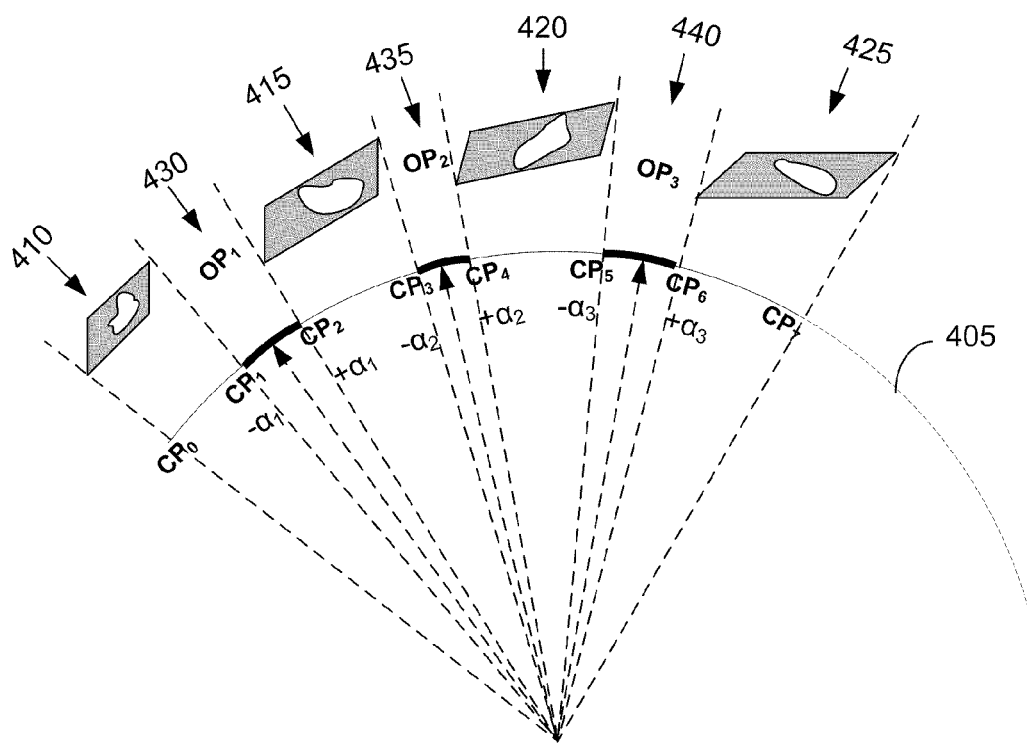
FIG. 4 is a depiction of some aspects of rotational radiation dose delivery according to some embodiments.

FIG. 4 is an illustrative depiction of some aspects of radiation dose delivery according to some embodiments. More particularly, FIG. 4 illustrates various aspects of a treatment plan that may be used for delivery of radiation treatment herein.

Arc 405 represents a path gantry 115 may traverse as the gantry rotates about a patient. In some aspects, treatment head 115 may deliver radiation to a patient area or volume of the patient, in accordance with a burst mode treatment plan, as gantry 115 rotates about the patient. In some embodiments, a burst mode treatment plan devised for treating patient 150 by radiation delivered by radiotherapy system 100 specifies a finite number of discrete control points (CPs) on arc 405. Burst mode radiation treatment scheme 400 includes a plurality of representative CPs—CP0, CP1, CP3, CP4, CP5, CP6, and CP7. Since gantry 115 continuously moves through arc 405 according to some embodiments herein, gantry 115 moves through the CPs without stopping at the CPs.

The burst mode treatment plan for treating patient 150 by burst mode radiation delivered by radiotherapy system 100 also specifies a finite number of discrete optimization points (OPs) on arc 405. Burst mode radiation treatment scheme 400 includes a plurality of representative OPs, e.g., OP1 at 430, OP2 at 435, and OP3 at 440. In some embodiments, each OP represents a treatment gantry angle at which a prescribed dose amount of radiation is to be delivered to the patient area, as specified by a burst mode treatment plan. Since gantry 115 continuously moves in a rotational manner around the patient according to some embodiments herein, gantry 115 moves through the OPs without stopping at the OPs. In some aspects, the burst mode treatment radiation is delivered around each OP since gantry 115 moves continuously. Radiation dose delivery may occur around OP by delivering the burst mode radiation (±α) each gantry treatment angle. This aspect of the burst mode treatment plan and radiation delivery scheme is illustrated in FIG. 4. In some embodiments, (±a) may vary from OP to OP. As illustrated in FIG. 4, $OP_1$ (430) includes ($\pm\alpha_1$), $OP_2$ (435) includes ($\pm\alpha_2$), and $OP_3$ (440) includes ($\pm\alpha_3$).

In some embodiments herein, a burst mode treatment plan may be provided for irradiating patient 150 involving radiation treatment that accounts for moving aspects of the radiotherapy system 100 and patient 150. The burst mode treatment plan specifies a number of control points that describe a dose distribution in space. The burst mode treatment plan also specifies for each dose a number of prescriptions for parameters (i.e., axes) that control a position, a direction, a shape, and an intensity of a treatment radiation beam and a position of the target volume. The burst mode treatment plan prescribes parameters for one or more dynamic axes, parameters for one or more static axes, and position parameters for the one or more dynamic axes corresponding to a prescribed delivery period of burst mode irradiation. As used to herein, dynamic axes refers to the one or more axes that controls at least one of a position, a direction, a shape, and an intensity of a treatment radiation beam and a position of the target volume according to the burst mode treatment plan and the one or more dynamic axes are continually in motion, including during the irradiating of the target volume during the synchronization. Furthermore, static axes refers to the one or more axes that control at least one of a position, a direction, a shape, and an intensity of a treatment radiation beam and a position of the target volume according to the burst mode treatment plan and the one or more static axes are not in motion during the irradiating of the target according to the burst mode treatment plan.

In some embodiments, the burst mode treatment plan includes at least one dynamic axis and at least one static axis, as described herein. Regarding the static parameters, the burst mode treatment plan contains only fixed point position(s) describing the static axes for when the treatment beam is ON (i.e., the static axes are still during a beam ON condition). For the dynamic parameters, the burst mode treatment plan contains multiple overlapping positions or a range of positions describing the dynamic axes for a treatment beam ON condition, as prescribed by the burst mode treatment plan. As used herein, the prescribed delivery period of burst mode irradiation describing the dynamic axes for when the treatment beam is ON is referred to herein as a burst window.

In accordance with embodiments herein, one or more axes of motion may be specified or defined by the burst mode treatment plan. While the example of FIG. 3 discusses the movement of the gantry as one of the dynamic axes that is constantly moving, including during a treatment beam ON period, other moveable components of the radiotherapy system 100 and the patient may be controlled to move as expressed by the dynamic axes parameters. In some embodiments, a number of axes of radiotherapy system 100 may be manipulated and moved to control a position, a direction, a shape, and an intensity of a treatment beam or a position of a patient. In some embodiments, gantry 115 may be controlled, as shown in the example of FIG. 3, to move or alter the position of a treatment beam. However, embodiments herein are not limited to movement related to the gantry. In some embodiments, support table 145 may be rotated or otherwise moved, arm 140 supporting imaging device 135 may be moved, treatment head 110, and other components of system 100 may be moved. In some embodiments, a position of patient 150 may be moved or varied.

Furthermore, the shape of the treatment radiation beam may be shaped by beam shaping device 80 (e.g., MLC leaves) at each OP. Also, the amount of dose of radiation to be delivered at each OP is modified and/or optimized based on the number of OPs and the radiation to be delivered to the patient area. The optimization may be done so that an aggregate of all OPs results in an optimum treatment plan.

In some aspects, a burst mode treatment therapy plan incorporates the constraint that a treatment opportunity and a prescribed delivery period of burst mode irradiation coincide in time. Accordingly, a gated burst mode radiotherapy system in accordance with embodiments herein may operate to synchronize the treatment opportunity and the prescribed delivery period of burst mode irradiation.

In some embodiments, a radiotherapy treatment planning professional may enter a radiotherapy prescription into a planning system that specifies the amount of dose radiation a targeted patient volume receive. The treatment plan may also specify a maximum dose of radiation that the organs at risk (OAR) are allowed to receive. Additional considerations and constraints of the treatment plan may also be specified or otherwise entered and included in the treatment plan planning system, as done in an inverse-planning system that may be used to create an optimum IMRT (intensity-modulated radiation therapy) plan.

In accordance with some aspects of the burst mode radiation treatment of moving targets herein, a planning system assumes the delivery of the radiation treatment is to be done by a continuously moving dynamic axes. Some of the parameters of the dynamic axes may have physical, practical, or other types of speed limitations that may be specified or otherwise accounted for in the planning system. Other operating limitations or constraints on, for example, beam shaping device 80 such as MLC leaf speed, may also be provided to the planning system. Furthermore, the prescribed dose rate and a specific period of time for delivering the treatment radiation may be provided to the burst mode treatment planning system. Based on such provided and specified information, the burst mode treatment planning system may create an optimum plan for burst mode radiation treatment of a moving patient area.

Based on a burst mode treatment plan considering at least some of the above discussed factors, radiotherapy system 100, including processor 175, may analyze the treatment plan to determine a speed for moving dynamic axes parameters between adjacent and consecutive CPs. The dynamic axes speed between two adjacent and consecutive CPs during which, for example, a beam shaping device is to be configured to accommodate delivery of a dose of treatment radiation may be determined such that beam shaping device 80 will reach a desired shape for delivery of a prescribed radiation treatment as the dynamic axes travel between the two CPs. Thus, the beam shaping device in this example is a static axis parameter since it is still during a treatment beam ON delivery period. Such a determination of the dynamic axis speed may consider the amount of leaf (i.e., 82/84 and 86/88) travels needed to obtain the desired beam shaping configuration and the effective leaf speed. The dynamic axes parameter speed between two adjacent and consecutive CPs during which a dose of radiation will be delivered (i.e., the burst window) may be determined such that a prescribed dose amount of radiation may be delivered to a patient area given the effective dose rate and the angular interval between the CPs.

Referring to FIG. 4, beam shaping device may be, for example, configured between CP0 and CP1 at 410, CP2 and CP3 at 415, CP4 and CP5 at 420, and CP6 and CP7 at 425 and held static during the burst windows. During these intervals of movement, the speed of one or more dynamic axes is adjusted such that beam shaping device 80 will reach the desired shape for delivery of a prescribed burst mode radiation treatment as the dynamic axes travels between the two adjacent and consecutive CPs. Still referring to FIG. 4, a dose of radiation treatment is delivered to a patient target volume dynamically during a burst window between CP1 and CP2 at 430, CP3 and CP4 at 435, and CP5 and CP6 at 440. The beam shaping device (i.e., static axis parameter) is held static during the burst windows.

During the burst windows 430, 435, and 440, the patient target volume should be in a position to accept being irradiated by the burst mode treatment beam. As introduced above, the time during which the target volume is in an acceptable position for being irradiated with the burst treatment beam is referred to as a treatment opportunity. In some embodiments, the treatment opportunity is substantially periodic based on the movement of the target volume being primarily attributed to the breathing cycles of patient 150. Referring to FIG. 3, the treatment windows may correspond to or track the time period the breathing cycle is between 80% and 100% exhalation.

During the burst windows 430, 435, and 440, the speed of the dynamic axes may be adjusted such the prescribed dose amount of radiation may be delivered to the patient area given the effective dose rate and the angular interval between the CPs.

In some embodiments, all of the static axes parameters (e.g., the beam shaping device in the current example, not limited thereto) reach their desired destination position before the occurrence of a next treatment opportunity. Since the static axes parameters may be specified by the burst treatment plan, each of the static axes parameters should reach their desired destination position in agreement with the burst mode treatment plan before the occurrence of the next treatment opportunity. Referring to FIGS. 3 and 4, the static axes may be moved during, for example period 410, to reach their designated positions per the burst mode treatment plan before the occurrence of the next treatment opportunity 341. In an instance additional time is required for the static axes to reach their prescribed position(s), then the next treatment opportunity (e.g., 342) may be skipped, wherein a burst mode of treatment radiation is not delivered during the treatment opportunity 342 but instead is delivered during a later, subsequent treatment opportunity when the static axes parameters are satisfied (e.g., treatment opportunity 343).

In some embodiments, a periodicity of a treatment opportunity is used to determine future occurrences of a treatment opportunity. For example, a statistical model may be developed, determined, or obtained that provides, at least in part, a mechanism to determine an optimal speed of the one or more dynamic axes (e.g., a moveable gantry, a moveable table, etc.) using historical statistics regarding the breathing cycle of a patient. The statistical model may be used to facilitate synchronizing the timing of treatment opportunities (i.e., the target volume is in the correct position for being irradiated per the burst treatment plan) and the burst windows (i.e., the prescribed delivery period of burst mode irradiation). Thus, the delivery of the burst mode treatment radiation may be structured according to the statistical model.

In some embodiments, a speed of the movement of the one or more dynamic axes may be controlled such that the prescribed delivery period of the burst mode irradiation or burst window coincides with a treatment opportunity. In some scenarios, a statistical model based on previous periodic breathing or otherwise induced target movements can be used to predict or forecast the timing of a next treatment opportunity. Based on the predicted next treatment opportunity, the speed of the one or more dynamic axes may be adjusted.

In some instances, the speed of the movement of the one or more dynamic axes may be increased when the position of at least one of dynamic axes is not within the burst window and the speed of the one or more dynamic axes is decreased when the position of at least one dynamic axis does coincide with the burst window. In this manner, the probability of successfully synchronizing the burst windows and the treatment opportunities to coincide might be increased by increasing or even maximizing the time of overlap between the treatment window and the burst window.

In accordance with aspects herein where the gated burst mode radiotherapy system operates to synchronize the treatment opportunity and the prescribed delivery period of burst mode irradiation or burst window, the speed of the one or more dynamic axes may be adjusted based on a continuously updated determination of the treatment opportunity such that the prescribed delivery period of the burst mode irradiation coincides with about a center of the treatment opportunity. Further still, the synchronizing of the treatment opportunity and the burst window may include stopping the motion of the one or more dynamic axes in an instance the treatment opportunity does not coincide with the burst window or the periodic treatment opportunity ends before an entirety of a prescribed dose can be delivered within the burst window. In some aspects, adjustments and considerations may be taken into account such that the motion of the one or more dynamic axes is stopped at about a midpoint or center of the burst window, if it is determined the dynamic axes are to be stopped. In some aspects, stopping the motion of the one or more dynamic axes that would normally move continuously, even during a beam ON period, may not be a most desired operating procedure. As an alternative, the speed of the dynamic axes may be increased or decreased as opposed to being completely stopped.

In some embodiments, the historical statistical model(s) disclosed herein may be used to control a synchronization between the treatment opportunity and a burst window, alone or in combination with other models, techniques, and mechanisms. In some embodiments, a historical statistical model may be used to establish, at least, baseline timing control parameters and other mechanisms like a real-time, ongoing predictive analysis model employing an analysis of a current breathing cycle may be used to make adjustments or refinements to the timing control parameters.

In some embodiments, a rate of dose delivery may change depending on the amount of dose that is to be delivered at each segment or at each OP±α. In some aspects, the dose rate will be set high to reduce treatment time for larger monitor unit (MU) values. For small MU values, the dose rate may be reduced to ensure accurate dose delivery, even though such a reduction of the dose rate may be achieved at some expense of a treatment time. In some aspects, and in an effort to reduce a treatment time, the radiation dose may be delivered in minimum amount of time (i.e., with maximum allowable dose rate).

Figure 5:
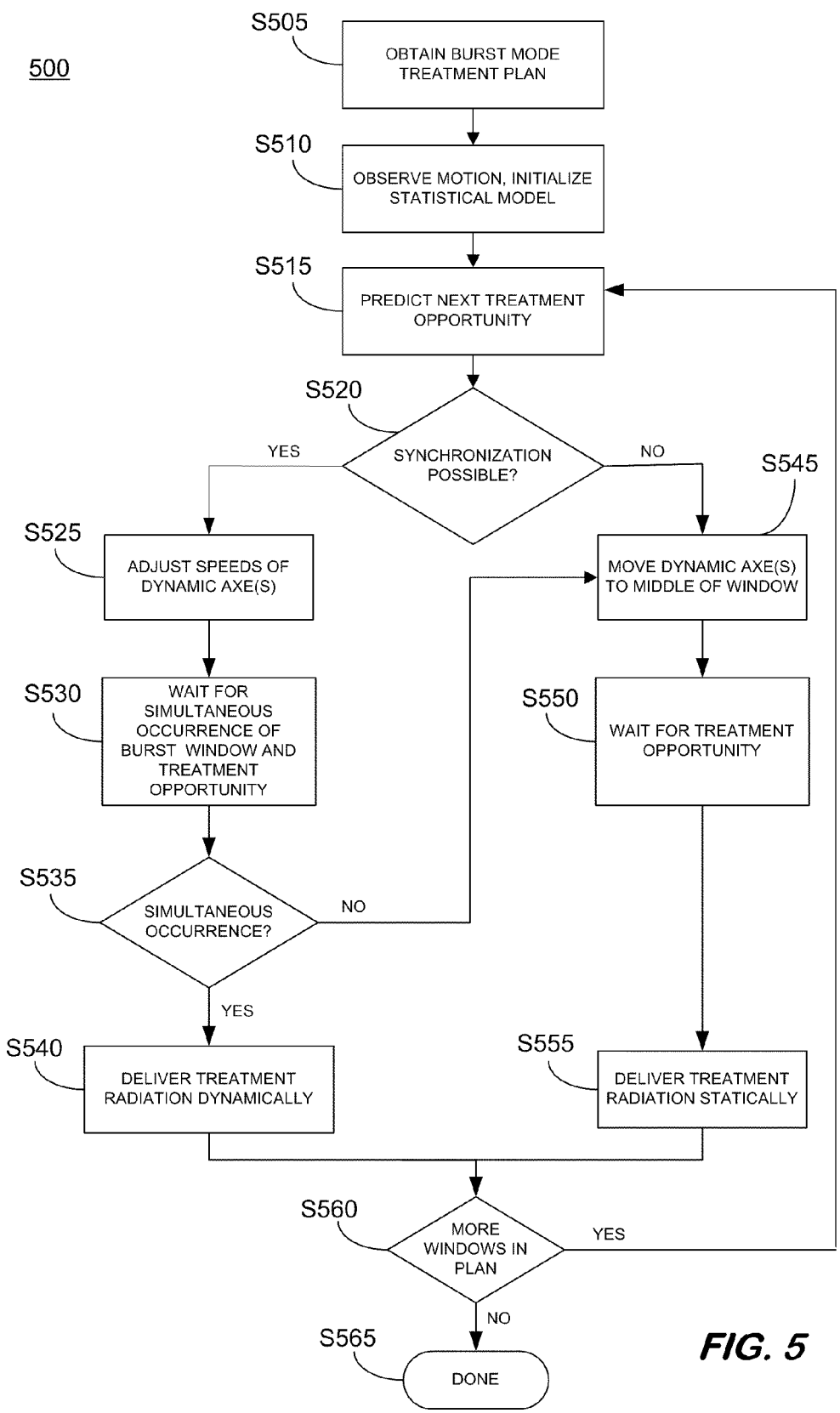
FIG. 5 is a flow diagram according to some embodiments.

FIG. 5 is a flow diagram of a process 500 to provide burst mode radiation treatment of moving targets according to some embodiments. Process 500 and the other processes described herein may be performed using any suitable combination of hardware, software or manual means. Software embodying these processes may be stored by any medium, including a fixed disk, a floppy disk, a CD-ROM, a DVD-ROM, an optical disk, a magnetic tape, a solid state storage device, or a signal. Examples of these processes will be described below with respect to the elements of radiotherapy treatment room 100, but embodiments are not limited thereto.

In some embodiments, and prior to S505, a burst mode treatment plan may be established. At S505, an operator may obtain the treatment plan. In some embodiments, the burst mode treatment plan, or parts thereof, may be determined and established at S505. At S510, an observation period of a patient may occur wherein multiple breathing cycles of the patient may be observed and measured over a period of time. A statistical analysis of the observed measurements of the patient's breathing may be used to determine a statistical model of the patient's breathing. Thereafter, the operator may interact with input device 165 of operator console 160 to initiate operation of linear accelerator 105 to receive and/or execute a burst mode radiotherapy treatment plan. In response to the user interaction, processor 175 may execute program code or instructions of a system control application stored in storage 180. The operator may further operate input device 165 to initiate radiation of a target volume or area (e.g., a tumor) of patient 150, including moving patient areas.

Some aspects of the burst mode radiation treatment may include moving one or more axes of system 100 (e.g., gantry 115, table 150, imaging device 135, etc.) and patient 150, according to the burst mode treatment plan. At S515, with the patient, gantry, imaging device, and other aspects of system 100 at positions for treatment, a prediction of a next treatment opportunity is performed. The prediction may be made based on the statistical model determined and initialized at S510. As explained above, the treatment opportunity refers to a period of time the target volume is in a position to be irradiated according to the burst mode treatment plan. Also, the burst mode treatment plan prescribes parameters for one or more dynamic axes, parameters for one or more static axes, and position parameters for the one or more dynamic axes corresponding to a prescribed delivery period of burst mode irradiation;

At S520, a determination is made whether the predicted next treatment opportunity and a burst window as prescribed by the burst mode treatment plan can be synchronized. In some instances, whether the next treatment opportunity and the prescribed burst window can be synchronized may be dependent on the actual breathing pattern of the patient and limitations of radiotherapy system 100. For example, in the instance the motion of the patient target volume is not consistently periodic, then synchronization at may not be possible. Patient 150 may not be breathing in a consistent manner for any number of reasons.

In some embodiments, patient 150 may be equipped with a bio-feedback device, as a means of assisting the patient to breathe in a consistent periodic manner.

In the instance it is determined that synchronization between the next treatment opportunity and the prescribed burst window is possible, then process 500 proceeds to S525 where an effort is made to synchronize the treatment opportunity and the prescribed delivery period of burst mode irradiation, for the simultaneous occurrence of the treatment opportunity and the burst window is a condition for dynamically delivering the burst mode radiation. Efforts to synchronize the next treatment opportunity and the prescribed burst window may include adjusting the speed at which the dynamic axes (potentially including, but not limited to, gantry 105) are moving. The speed of the dynamic axes may be increased and decreased by varying amounts in an attempt to synchronize the treatment opportunity and the prescribed burst window.

At S530, process 500 waits for the simultaneous occurrence of the treatment opportunity and the prescribed burst window. While it may be anticipated that the next treatment opportunity and the prescribed burst window will occur simultaneously based on the adjustment of the dynamic axes at S525 and consideration of the statistical model of the patient's breathing, a determination is made at S535 whether the next treatment opportunity and the prescribed burst window actually overlap or occur simultaneously.

In some embodiments, the adjustment of the dynamic axes speed(s) may optionally be based on real time prediction updates. For example, based on on-going observations, the adjustments determined and used at S525 may be augmented or supplemented with real time prediction updates.

In the instance the next treatment opportunity and the prescribed burst window actually overlap or occur simultaneously, process 500 proceeds to S540 for the dynamic delivery of the burst mode treatment radiation, in the dose prescribed by the burst mode treatment plan. Accordingly, the dynamic axes of the radiotherapy treatment system continues to move as the treatment radiation is delivered to the patient at S540.

Returning to S520 where it is determined whether it is possible for the next treatment opportunity and the burst window to be synchronized (e.g., due to breathing of patient, physical constraints on speed of radiotherapy system, etc.), process 500 proceeds to S545 in the instance synchronization is not possible. At S545, the dynamic axes are moved to a set or fixed position. In some embodiments, the dynamic axes may be moved to and stopped at a position determined to be within the burst window. This action may happen when the treatment opportunity will end before the entirety of a prescribed dose can be delivered within the burst window or in instances the treatment opportunity does not coincide with the burst window (i.e., from S535).

From S545, process 500 waits for the treatment opportunity with the dynamic axes set at fixed or static position(s). Upon the occurrence of the treatment window, process 500 proceeds to S555 for the static delivery of the burst mode treatment radiation, in the dose prescribed by the burst mode treatment plan. While the dynamic axes of the radiotherapy treatment system do not continue to move as the treatment radiation is delivered to the patient at S555, the proper dose is delivered to the target when the target is in the proper position to receive the burst mode treatment radiation.

At the conclusion of the burst mode radiation treatment delivery at S540 or S555, a determination is made at S560 whether the treatment plan includes additional prescribed burst windows for radiation delivery. If no more treatment windows are prescribed, then process 500 may terminate at S565. Otherwise the process may return to S515 where a next treatment opportunity is predicted for further radiation treatment delivery. In some embodiments, the further predictions may be made based on a continuously updated statistical model that considers updated historical data related to the patient's breathing behavior.

Figure 6:
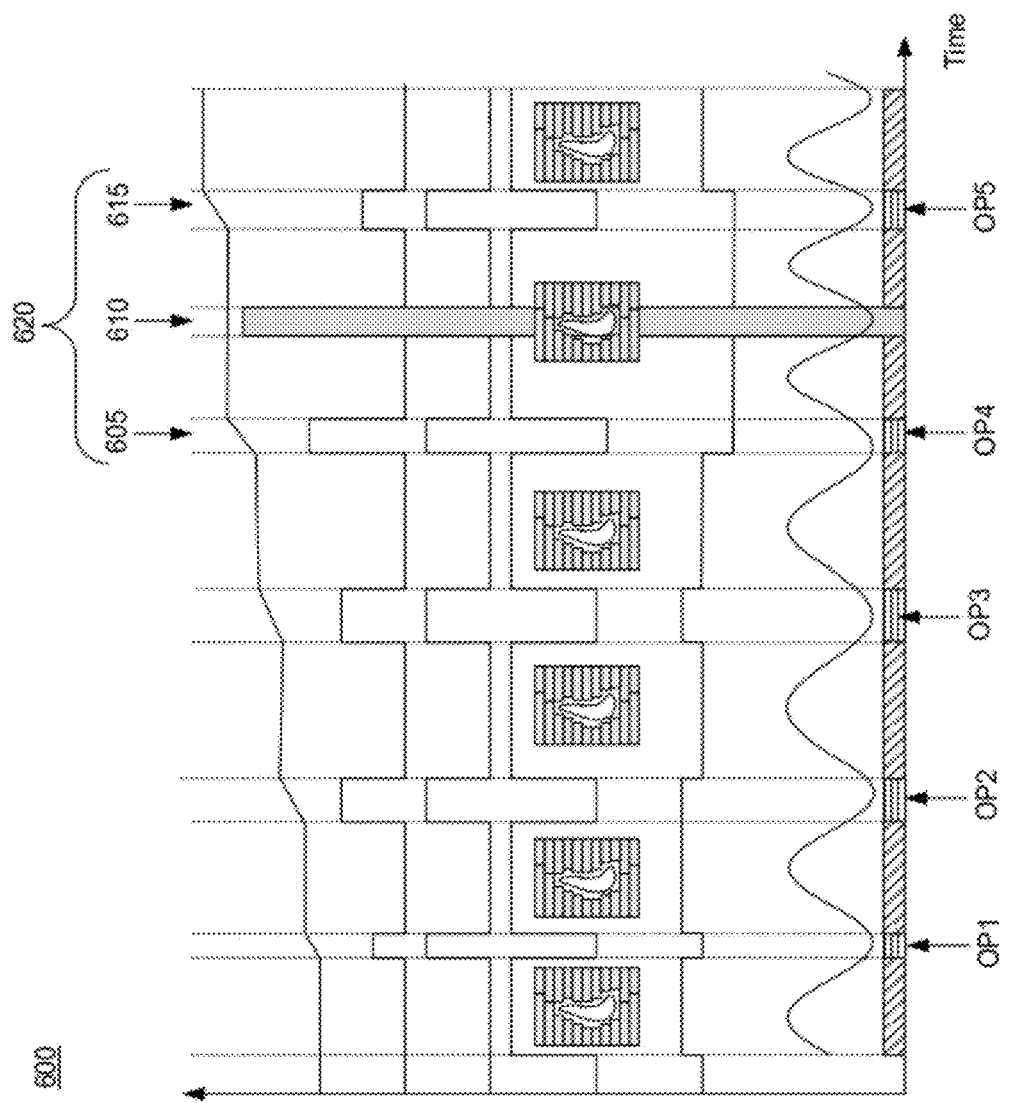
FIG. 6 is a timing diagram according to some embodiments.

FIG. 6 is a timing diagram 600 according to some embodiments. Gantry speed is shown at 605, beam shaping device motion is shown at 610, radiation delivery is shown at 615, a dose rate is shown at 620, and an accumulated dose is depicted at 625. As illustrated, gantry 115 ramps up at time period 630 and ramps down at time period 675. Further illustrated are the time periods during which beam shaping device 80 is moved, adjusted, or otherwise configured to a shape required for an upcoming delivery of treatment radiation. These beam shaping movements occur in time periods or intervals 635, 645, 655, and 665. As depicted at 680, 685, 690, and 695, beam shaping device 80 is dynamically adjusted per the treatment plan to accommodate the different patient areas or volumes presented at the different OPs. FIG. 6 also shows gantry 115 continuously moves after ramping up and before ramping down.

Further illustrated in timing diagram 600 are the time periods during which treatment radiation is delivered to a moving patient area. These periods of treatment radiation delivery occur in time periods or intervals 640, 650, 660, and 670. It is noted that the treatment radiation is delivered between two adjacent and consecutive CPs and at/around an OP located between the two adjacent and consecutive CPs.

FIG. 6 is timing diagram according to some embodiments. Timing diagram 600 illustrates a delaying of treatment in response to a fluctuation in the breathing of patient 150. In particular, the breathing by patient 150 increases at region 620. In response to the increased rate of breathing, burst mode treatment radiation is not delivered during the next treatment opportunity 660 after treatment opportunity 605 but is instead delayed to until a future treatment opportunity 615 presents itself. An adjustment to the speed of one or more of the dynamic axes (e.g., gantry 115, but not limited thereto) is consistent with process 500, but not limited thereto.

The several embodiments described herein are solely for the purpose of illustration. Therefore, persons in the art will recognize from this description that other embodiments may be practiced with various modifications and alterations.

What is claimed is:

1. A method comprising:
obtaining a burst mode treatment plan to be administered by a radiotherapy device, the burst mode treatment plan prescribing parameters for one or more dynamic axes, parameters for one or more static axes, and position parameters for the one or more dynamic axes corresponding to a prescribed delivery period of burst mode irradiation;
receiving an indication of occurrences of a substantially periodic treatment opportunity for a target volume of a patient from a gating device, the treatment opportunity being a period of time the target volume is in a position to be irradiated according to the burst mode treatment plan;
synchronizing the treatment opportunity and the prescribed delivery period of burst mode irradiation; and
irradiating the target volume during the synchronization of the treatment opportunity and the prescribed delivery period of burst mode irradiation.

2. The method of claim 1, wherein the one or more dynamic axes controls at least one of a position, a direction, a shape, and an intensity of a treatment radiation beam and a position of the target volume according to the burst mode treatment plan and the one or more dynamic axes are continually in motion, including during the irradiating of the target volume during the synchronization.

3. The method of claim 1, wherein the one or more static axes controls at least one of a position, a direction, a shape, and an intensity of a treatment radiation beam and a position of the target volume according to the burst mode treatment plan and the one or more static axes are not in motion during the irradiating of the target volume during the synchronization.

4. The method of claim 1, wherein the one or more dynamic axes includes at least one movable physical component of the radiotherapy device other than a gantry.

5. The method of claim 1, wherein a periodicity of the treatment opportunity is used to determine future occurrences of a treatment opportunity.

6. The method of claim 5, wherein each of the one or more static axes are positioned in agreement with the burst mode treatment plan before an occurrence of a next treatment opportunity.

7. The method of claim 5, wherein a speed of a movement of the one or more dynamic axes is controlled such that the prescribed delivery period of the burst mode irradiation coincides with a treatment opportunity.

8. The method of claim 1, wherein a speed of a movement of the one or more dynamic axes is increased when a position of at least one of the dynamic axes does not coincide with the prescribed delivery period of the burst mode irradiation and the speed of the movement of the one or more dynamic axes is decreased when the position of at least one of the dynamic axes does coincide with the prescribed delivery period of the burst mode irradiation.

9. The method of claim 8, wherein the speed of the movement of the one or more dynamic axes is adjusted based on a continuously updated determination of the treatment opportunity such that the prescribed delivery period of the burst mode irradiation coincides with about a center of the treatment opportunity.

10. The method of claim 1, wherein the synchronizing of the treatment opportunity and the prescribed delivery period of the burst mode irradiation comprises stopping the motion of the one or more dynamic axes in an instance the treatment opportunity does not coincide with the prescribed delivery period of the burst mode irradiation or the periodic treatment opportunity ends before an entirety of a prescribed dose can be delivered within the prescribed delivery period of the burst mode irradiation, whether realized or predicted.

11. The method of claim 9, wherein the motion of the one or more dynamic axes is stopped at about a midpoint of the prescribed delivery period of the burst mode irradiation.

12. A system comprising:
one or more moveable axes of a radiotherapy device other than a rotatable radiotherapy gantry;
an emission device mounted to the radiotherapy gantry to emit a treatment radiation beam; and
a processor to:
obtain a burst mode treatment plan to be administered by a radiotherapy device, the burst mode treatment plan prescribing parameters for the one or more dynamic axes, parameters for one or more static axes, and position parameters for the one or more dynamic axes corresponding to a prescribed delivery period of burst mode irradiation;
receive an indication of occurrences of a substantially periodic treatment opportunity for a target volume of a patient from a gating device, the treatment opportunity being a period of time the target volume is in a position to be irradiated according to the burst mode treatment plan;
synchronize the treatment opportunity and the prescribed delivery period of burst mode irradiation; and irradiate the target volume during the synchronization of the treatment opportunity and the prescribed delivery period of burst mode irradiation.

13. The system of claim 12, wherein the one or more dynamic axes controls at least one of a position, a direction, a shape, and an intensity of a treatment radiation beam and a position of the target volume according to the burst mode treatment plan and the one or more dynamic axes are continually in motion, including during the irradiating of the target volume during the synchronization.

14. The system of claim 12, wherein the one or more static axes controls at least one of a position, a direction, a shape, and an intensity of a treatment radiation beam and a position of the target volume according to the burst mode treatment plan and the one or more static axes are not in motion during the irradiating of the target volume during the synchronization.

15. The system of claim 12, wherein the one or more dynamic axes includes at least one movable physical component of the radiotherapy device other than a gantry.

16. The system of claim 12, wherein a periodicity of the treatment opportunity is used to determine, by the processor, future occurrences of a treatment opportunity.

17. The system of claim 16, wherein each of the one or more static axes are positioned by the processor in agreement with the burst mode treatment plan before an occurrence of a next treatment opportunity.

18. The system of claim 16, wherein a speed of a movement of the one or more dynamic axes is controlled by the processor such that the prescribed delivery period of the burst mode irradiation coincides with a next treatment opportunity.

19. The system of claim 12, wherein a speed of a movement of the one or more dynamic axes is increased by the processor when a position of at least one of the dynamic axes does not coincide with the prescribed delivery period of the burst mode irradiation and the speed of the movement of the one or more dynamic axes is decreased by the processor when the position of at least one of the dynamic axes does coincide with the prescribed delivery period of the burst mode irradiation.

20. The system of claim 19, wherein the speed of the movement of the one or more dynamic axes is adjusted based on a continuously updated determination of the treatment opportunity such that the prescribed delivery period of the burst mode irradiation coincides with about a center of the treatment opportunity.

21. The system of claim 19, wherein the motion of the one or more dynamic axes is stopped at about a midpoint of the prescribed delivery period of the burst mode irradiation.

22. The system of claim 12, wherein the synchronizing of the treatment opportunity and the prescribed delivery period of the burst mode irradiation comprises the processor stopping the motion of the one or more dynamic axes in an instance the treatment opportunity does not coincide with the prescribed delivery period of the burst mode irradiation or the periodic treatment opportunity ends before an entirety of a prescribed dose can be delivered within the prescribed delivery period of the burst mode irradiation, whether realized or predicted.

* * * * *